US00PP27098P3

(12) United States Plant Patent
Denis

(10) Patent No.: US PP27,098 P3
(45) Date of Patent: Aug. 23, 2016

(54) ***CALATHEA* PLANT NAMED 'BICA146'**

(50) Latin Name: ***Calathea* spp.**
Varietal Denomination: BICA146

(71) Applicant: Rene Denis, Beervelde (BE)

(72) Inventor: Rene Denis, Beervelde (BE)

(73) Assignee: Denis—Plants B.V. (BE)

( * ) Notice: Subject to any disclaimer, the term of this patent is extended or adjusted under 35 U.S.C. 154(b) by 129 days.

(21) Appl. No.: 13/999,859

(22) Filed: Mar. 28, 2014

(65) Prior Publication Data

US 2015/0282414 P1 Oct. 1, 2015

(51) Int. Cl.
*A01H 5/00* (2006.01)

(52) U.S. Cl.
USPC ..... Plt./375

(58) Field of Classification Search
USPC ..... Plt./375
See application file for complete search history.

*Primary Examiner* — Keith Robinson

(57) ABSTRACT

A new and distinct *Calathea* cultivar named 'BICA146' is disclosed, characterized by purple-white flowers, unique leaf texture and coloration. The new variety is a *Calathea*, typically produced as an indoor ornamental plant.

2 Drawing Sheets

Latin name of the genus and species: *Calathea* spp.
Variety denomination: 'BICA146'.

BACKGROUND OF THE INVENTION

This application relates to a new cultivar of *Calathea*. The new variety is the product of chance discovery, by the inventor, Rene Denis. The new variety originated as a naturally occurring whole plant mutation from the unpatented commercial variety *Calathea* 'Gekko Pink'.

The new variety was first selected by the inventor, in the breeder's commercial greenhouse in Lochristi, Belgium during the Fall of 2009. After identifying the new variety as a potentially interesting selection, the inventor continued confidential testing and propagation of 'BICA146', assessing stability of the unique characteristics of this variety.

Asexual reproduction of the new cultivar 'BICA146' was first performed in a commercial laboratory in Belgium by tissue culture in December of 2010. Access to all plants was restricted, as plants were kept in a greenhouse not open to the public. Through subsequent propagation, many generations have been reproduced, which have shown that the unique features of this cultivar are stable and reproduced true to type.

SUMMARY OF THE INVENTION

The cultivar 'BICA146' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BICA146'. These characteristics in combination distinguish 'BICA146' as a new and distinct *Calathea* cultivar:

1. Purple-white flower color.
2. Leaf texture.
3. Leaf coloration.

PARENT COMPARISON

Plants of the new cultivar 'BICA146' are similar to the parent in most horticultural characteristics. However the new variety, 'BICA146' differs from the 'Gekko Pink' in the following characteristics:

1. Darker flower color.
2. Young inflorescence is much darker.

COMMERCIAL COMPARISON

'BICA146' can be compared to the commercial variety *Calathea* 'Mamba Pink', unpatented. While *Calathea* 'Bica146' and *Calathea* 'Mamba Pink' are similar in most horticultural characteristics, the new variety differs in the following;

1. The new variety has a wider greyed-green leaf margin than 'Mamba Pink'.
2. Coloration of the main leaf vein of the new variety is lighter green than the main vein coloration of 'Mamba Pink'.
3. Petal base of the new variety is tinged red, whereas petal bases of 'Mamba Pink' are untinged.
4. Leaf margins of the new variety are less undulating than leaf margins of 'Mamba Pink'.
5. Coloration of the mature leaf underside of the new variety has no greyed-purple, whereas the mature leaf underside of 'Mamba Pink' is significantly colored with greyed-purple.
6. Overall leaf coloration of the new variety is lighter, with more greyed-green than overall leaf coloration of 'Mamba Pink'.

BRIEF DESCRIPTION OF THE PHOTOGRAPH

The accompanying photographs illustrate in full color a typical plant of 'BICA146' grown in a commercial greenhouse in Beervelde, Belgium. The plant is 10 months old from a rooted cutting, in a 17 cm pot.

Figure 1:
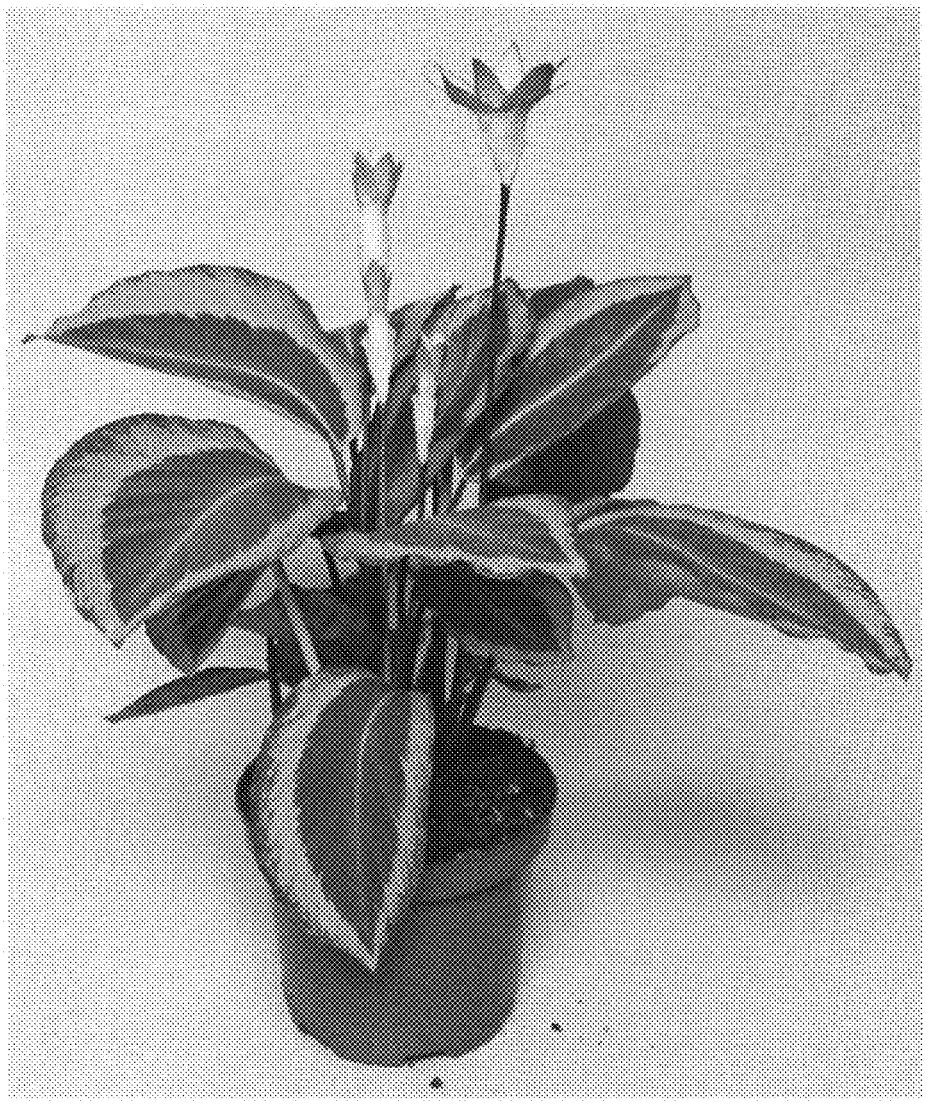
FIG. 1 is the entire plant.
Figure 2:
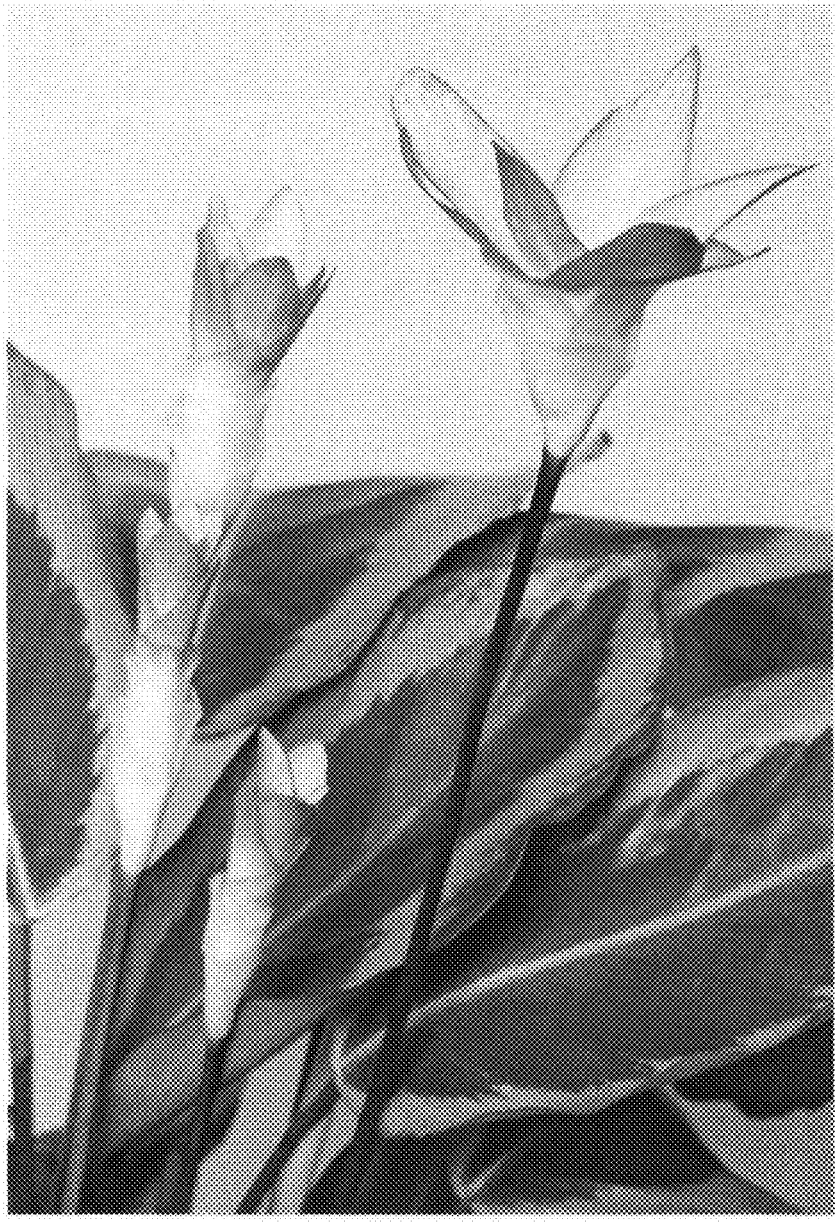
FIG. 2 is a close up of the flowers.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe a typical plant of 'BICA146' grown in a commercial greenhouse in Beervelde, Belgium. The plant is 231 days old from a rooted cutting, in a 17 cm pot. Temperatures ranged between 21° C. and 26° C. (ideally 26° C.) during the day 19° C. and 23° C. (ideally 23° C.) at night. The ideal growing conditions for this variety could not be met because of various reasons resulting in a slightly shorter plant size than under ideal conditions. Supplemental lighting was given. Artificial lighting of 14 hours a day from cutting to end of finished plant (minimum of 3700 lux). Measurements and numerical values represent averages of typical plant types.

Botanical classification: *Calathea* spp. 'BICA146'.

PROPAGATION

First propagation method: Tissue culture.

Time to initiate roots:

*Summer.*—14 to 16 days at approximately 21° C.

*Winter.*—15 to 17 days at approximately 21° C.

Time to produce a rooted plant: Approximately 4 to 6 weeks, then about 40 weeks to a flowering plant.

Root description: Non-fleshy, moderately fibrous, densely branched, colored grey-brown, near RHS N199B.

PLANT

Growth habit: Tender annual, typically used for indoor ornamental purposes. Overall plant shape is broad obovate, top flattened.

Height: Average: 39.0 cm.

Plant spread: Average: 44.0 cm.

Growth rate: Moderate.

Main stem: No main stems present, leaves grow in basal rosettes.

Branching characteristics: No main or lateral stems present, leaves grow in basal rosettes.

FOLIAGE

Leaf:

*Arrangement.*—Distichous.

*Quantity.*—Approximately 4 per main rosette.

*Average length.*—19.0 cm (excl. petiole).

*Average width.*—10.7 cm.

*Shape of blade.*—Unequal broad elliptic to unequal broad obovate.

*Apex.*—Abruptly acute.

*Base.*—Rounded.

*Margin.*—Entire, slightly to moderately wavy.

*Texture of top surface.*—Glabrous, moderately glossy.

*Texture of bottom surface.*—Smooth, glossy, leathery.

*Pubescence.*—No leaf pubescence.

*Aspect.*—Petioles in an average angle of 80° (0°=horizontal); leaf-bases in an average angle of 30° to horizontal, leaf-tips pointed downward in an average angle of −50° to horizontal.

*Color.*—Young foliage upper side: Yellow-green; near RHS 145A, margins lighter; near RHS 149D, outer edge flushed darker; near RHS 145A and 145B. Young foliage under side: Yellow-green; in between near RHS 145A and 147D, margins lighter; near RHS 144D, outer edge flushed darker; in between near RHS 145A and 147D. Mature foliage upper side: Green; near RHS 143A but much darker, blotched lighter along the main vein; near RHS 143A and 143B, margins greyed-green; 191B, outer edge green; near RHS 143A but much darker. Mature foliage under side: Greyed-green; in between near RHS 189A and 191A, margins green to greyed-green; in between near RHS 138B and 191B.

*Venation.*—Type: Pinnate. Venation color upper side: Yellow-green; near RHS 146D. Venation color under side: Yellow-green; near RHS 152D.

*Petiole.*—Length: Average 15.8 cm (excl. geniculum). Diameter: Average: 0.4 cm. Color: Yellow-green; near RHS 152A to 152B. Texture: Glabrous, moderately glossy. Strength: Very strong, flexible.

*Petiole sheath.*—Present: Yes. Length: Average: 10.7 cm. Diameter: Average: 0.5 cm. Color: Transparent yellow-green; near RHS 152D.

*Geniculum.*—Present: Yes. Shape: Rounded, glabrous, slightly glossy. Length: Average: 2.4 cm. Diameter: Average: 0.45 cm. Color: Yellow-green; near RHS 152A.

FLOWER

Flowering characteristics: Inflorescences grow from the centers of the stems.

Days to flowering from rooted cutting: 33 weeks

Inflorescence and flower type and habit: Inflorescence upright, consisting of an average of 7 colorful bracts and an average of 7 whitish-colored lower bracts with small, individual flowers in between. Average inflorescence height: 7.0 cm. Average inflorescence width: 6.2 cm. Average 4 flowers per inflorescence. Flower shape: Cupped. Flower Aspect: Upright. Upper bracts shaped ovate, average length: 4.0 cm, average width: 2.0 cm, upper side colored purple; near RHS 75C, margins red-purple; near RHS 72A to 72B. Under side colored red-purple; near RHS 72C. Lower bracts shaped obcordate, average length: 3.1 cm, average width: 3.7 cm, both sides colored white; near RHS NN155D, base darker; near RHS NN155A.

Rate of flower opening: 20 to 30 days from bud to fully opened flower.

Flower longevity on plant: Average: 15 days.

Quantity of buds and flowers per plant: Average: 4 inflorescences.

Persistent or self-cleaning: Persistent.

Bud:

*Shape.*—Narrow oblong.

*Length.*—2.2 cm.

*Diameter.*—0.7 cm.

*Color.*—White; near RHS NN155D, base darker; near RHS NN155A.

Flower size:

*Diameter*.—Inflorescence: 1.3 cm.

*Depth*.—Inflorescence: 2.5 cm.

Petals (tepals):

*Quantity*.—Average: 4.

*Arrangement*.—Rotate (cruciform), upper tepal differs from lateral and lower tepal in size and colour.

*Length*.—2.7 cm

*Width*.—Upper tepal average 0.7 cm, lateral and lower tepals average 0.4 cm.

*Shape*.—Lower 75% fused in a tube, upper (free) 25% shaped Obcordate.

*Apex*.—Upper tepal broad acute, lateral and lower tepals acute.

*Base*.—Fused.

*Margin*.—Entire.

*Texture, upper and lower surfaces*.—Both sides glabrous and slightly glossy.

*Color*.—When opening, upper surface: White; near RHS NN155B, upper tepal striped and tinged red-purple; near RHS 71A and 72A. When opening, lower surface: White; near RHS NN155B, upper tepal striped and tinged red-purple; near RHS 72A. Fully opened, upper surface: White; near RHS NN155B, upper tepal striped and tinged red-purple; near RHS 71A and 72A. Fully opened, lower surface: White; near RHS NN155B, upper tepal striped and tinged red-purple; near RHS 72A.

Sepals: No sepals present.

Peduncles:

*Length*.—29.8 cm.

*Diameter*.—0.3 cm.

*Angle*.—About 0° to the lateral branch (=vertical).

*Strength*.—Moderately strong.

*Texture*.—Glabrous, moderately glossy.

*Color*.—Greyed-green; near RHS 195A.

Fragrance: No fragrance.

REPRODUCTIVE ORGANS

Stamens:

*Number*.—Average: 2.

*Filament length*.—Approximately 0.7 cm.

Anthers:

*Shape*.—Oblong.

*Length*.—Approximately 0.2 cm.

*Color*.—White; near RHS NN155B.

*Pollen*.—Color: Yellow; near RHS 11D. Quantity: Low.

Pistil:

*Number*.—Average: 1.

*Length*.—Average: 0.8 cm.

*Style*.—Length: 0.1 cm. Diameter: Less than 0.1 cm. Color: White; near RHS NN155B. Stigma: Shape: Acute. Color: White; near RHS NN155B. Ovary Color: White; near RHS NN155B. Ovary Diameter: Approximately 0.5 cm. Ovary Length: Approximately 0.6 cm.

OTHER CHARACTERISTICS

Seeds and fruits: No seeds/fruits detected to date.

Disease/pest resistance: Neither resistance nor susceptibility to the normal diseases and pests of *Calathea* have been observed. Well known foliar disease is bacterial leaf spot, caused by various species of *Cercospora, Bipolaris Botrytis* and *Pseudomonas cichorii*. An increasingly common foliar pathogen is *Drechslera setariae*. Typical root disease is caused by *Fusarium oxysporum*. Pests typical to *Calathea* include the Nematode *Radopholus simili*;. Mites; *Steneotarsonemus furcatus*; various flies in the *Mycetophilidae* and *Sciaridae* families as well as various species of *Aphis*.

Temperature tolerance: 17-30 degrees Celsius.

What is claimed is:

1. A new and distinct cultivar of *Calathea* plant named 'BICA146' as herein illustrated and described.

* * * * *